(12) United States Patent
Kamono

(10) Patent No.: US 8,059,257 B2
(45) Date of Patent: Nov. 15, 2011

(54) EXPOSURE APPARATUS AND DEVICE MANUFACTURING METHOD

(75) Inventor: Takashi Kamono, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 493 days.

(21) Appl. No.: 11/845,506

(22) Filed: Aug. 27, 2007

(65) Prior Publication Data

US 2008/0055574 A1 Mar. 6, 2008

(30) Foreign Application Priority Data

Sep. 4, 2006 (JP) ................. 2006-239551

(51) Int. Cl.
*G01N 21/00* (2006.01)
*G03B 27/32* (2006.01)
*G03B 27/42* (2006.01)
*G03B 27/52* (2006.01)
*G03B 27/58* (2006.01)

(52) U.S. Cl. ........... 355/30; 355/53; 355/72; 355/77; 356/237.1; 356/237.2; 356/237.3; 356/237.4; 356/237.5

(58) Field of Classification Search .......... 355/27, 355/30, 53, 77, 72, 75; 356/237.1–237.6; 427/8

See application file for complete search history.

(56) References Cited

U.S. PATENT DOCUMENTS

| 7,342,640 B2 * | 3/2008 | Kamono | 355/53 |
| 2006/0007419 A1 * | 1/2006 | Streefkerk et al. | 355/53 |
| 2006/0257553 A1 * | 11/2006 | Ohta et al. | 427/8 |
| 2007/0159609 A1 * | 7/2007 | Takaiwa et al. | 355/53 |
| 2007/0268466 A1 * | 11/2007 | Antonius Leenders et al. | 355/30 |

FOREIGN PATENT DOCUMENTS

| EP | 1672681 A1 | 6/2006 |
| JP | 06-124873 A | 5/1994 |
| JP | 2002-057100 A | 2/2002 |
| WO | 99/49504 A1 | 9/1999 |
| WO | 2005/036621 A1 | 4/2005 |
| WO | WO 2005076321 A1 * | 8/2005 |

* cited by examiner

*Primary Examiner* — Hung Henry Nguyen
*Assistant Examiner* — Colin Kreutzer
(74) *Attorney, Agent, or Firm* — Canon U.S.A., Inc., IP Division

(57) ABSTRACT

An exposure apparatus includes a projection optical system configured to project light from an original, wherein the apparatus exposes a substrate to light through liquid filled in a gap between the last surface of the projection optical system and the substrate; and a detecting device configured to detect a droplet adhering to the exposed substrate. The detecting device includes a storage unit configured to prestore first image data corresponding to a surface of the substrate without the liquid and an image-capturing unit configured to capture an image of a surface of the exposed substrate. The detecting device detects the droplet based on a comparison between the first image data and second image data obtained by the image-capturing unit.

10 Claims, 12 Drawing Sheets

WAFER SCAN DIRECTION

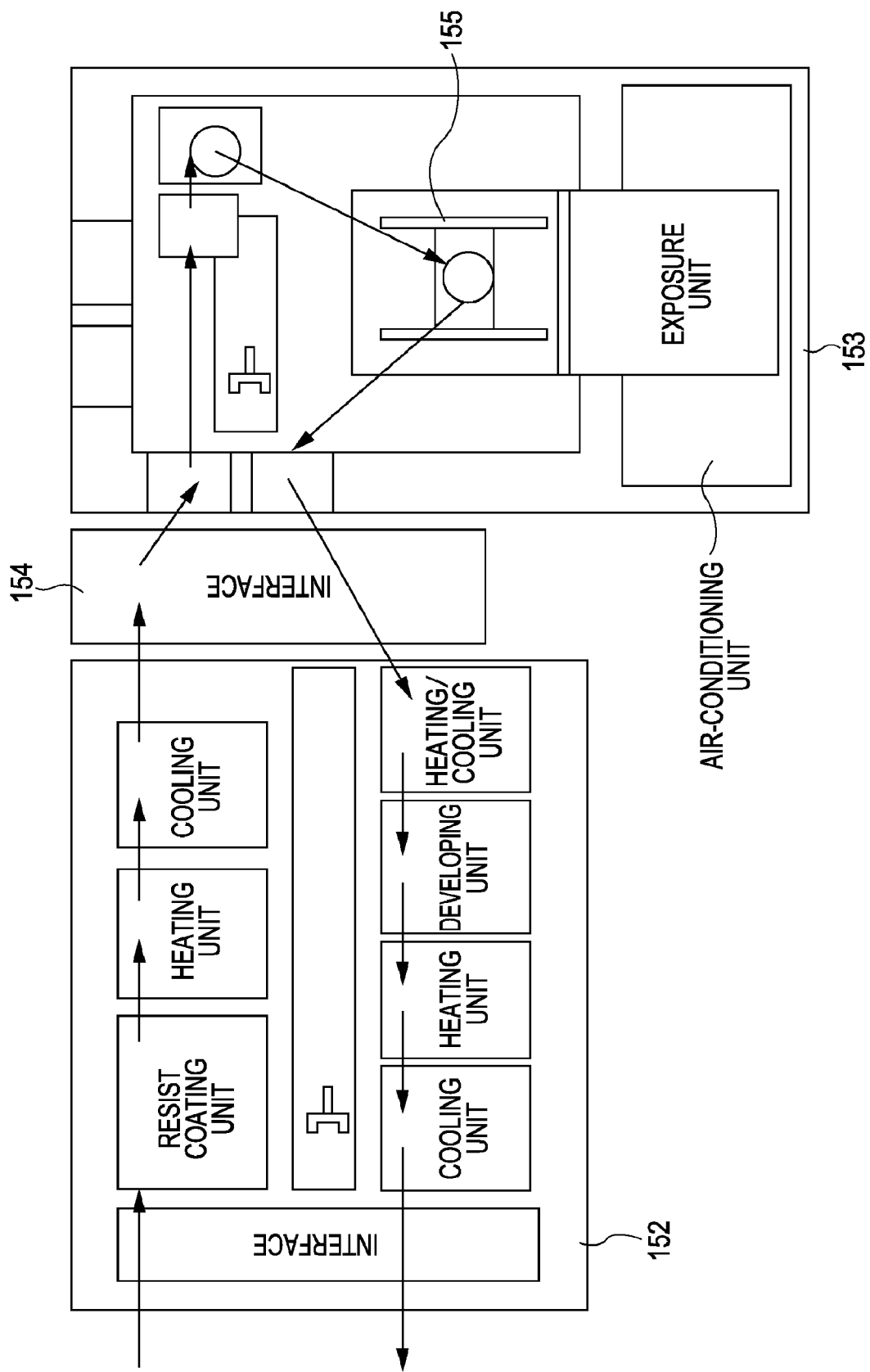

EXPOSURE APPARATUS AND DEVICE MANUFACTURING METHOD

BACKGROUND OF THE INVENTION

1. Field of the Invention

The present invention relates to liquid immersion exposure technology used in a process of manufacturing a device, such as a semiconductor device.

2. Description of the Related Art

A reduction projection exposure apparatus is used in manufacturing a semiconductor device (e.g., a large-scale integrated (LSI) circuit or very-large-scale integrated (VLSI) circuit) having an ultra-fine pattern. The reduction projection exposure apparatus projects, in a reduced size, a pattern formed on a mask onto a substrate coated with a photosensitive agent and transfers the pattern to the substrate. As the degree of integration in semiconductor devices increases, it becomes necessary to produce finer circuit patterns. With the development of resist processes, efforts have been made to develop exposure apparatuses that can achieve finer patterning.

A typical method for increasing the resolution of an exposure apparatus is to shorten the exposure wavelength or to increase the numerical aperture (NA) of a projection optical system. As for the exposure wavelength, there is an ongoing shift from the use of a 365-nm i-line to the use of light emitted from a KrF excimer laser having an oscillation wavelength of about 248 nm. Additionally, an ArF excimer laser having an oscillation wavelength of about 193 nm is under development. A fluorine ($F_2$) excimer laser having an oscillation wavelength of about 157 nm is also under development.

At the same time, a projection exposure method using a liquid immersion method is now gaining attention. The liquid immersion method is also a technique for increasing resolution, but is completely different from the other methods described above. In conventional methods, a space between the last surface of a projection optical system and a substrate surface (e.g., wafer surface) to be exposed is filled with a gas. However, in the liquid immersion method, projection exposure is performed while this space is filled with a liquid. An advantage of the liquid immersion method is that if the refractive index of a liquid filling the space between a projection optical system and a wafer is "n", it is possible to achieve a resolution that is "n" times higher than that achievable by conventional methods which uses light sources having the same wavelength as that of a light source used in the liquid immersion method. When, for example, the space between the projection optical system and the wafer is filled with pure water (having a refractive index of 1.33), if the maximum angle of incidence of a light beam forming an image on the wafer in the liquid immersion method is the same as that in the conventional methods, a resolution achieved by the liquid immersion method is 1.33 times higher than that achieved by the conventional methods even if the wavelength of the light source used in the liquid immersion method is the same as that of the light sources used in the conventional methods. This is equivalent to increasing the NA of the projection optical system in the conventional methods to 1.33 times. The liquid immersion method can achieve a resolution corresponding to an NA of 1 or more, which is not achievable by the conventional methods.

Examples of conventional exposure apparatuses to which the liquid immersion method is applied include an exposure apparatus disclosed in Japanese Patent Laid-Open No. 6-124873. FIG. 9A and FIG. 9B illustrate a structure of this exposure apparatus. In the exposure apparatus of FIG. 9A, filling a liquid tank (chamber) 109 with a liquid 130 allows the space between the last surface (optical element 107) of a projection optical system 104 and a wafer 102 to be filled with the liquid 130. In the liquid tank 109, there are disposed all or part of coarse positioning units 111-1 to 111-4 as well as a wafer conveying unit for conveying the wafer 102 from a wafer cassette 110 and placing the wafer 102 on a wafer chuck 112. The wafer chuck 112, an XY stage 113, and a fine-motion stage 114 are also disposed in the liquid tank 109. In FIG. 9A, a reference mirror 116 is attached in the X and Y directions (Y direction is not shown) to the fine-motion stage 114 and reflects light from a laser interferometer 115 to measure the position of the fine moving stage 114. The liquid tank 109 has a window 117 which allows light from the laser interferometer 115 to pass therethrough. A heat insulator 118 outside the liquid tank 109 thermally insulates the liquid tank 109 from outside.

Upon completion of exposure of the entire surface of the wafer 102 to light in the exposure apparatus of FIG. 9A, a conveying pump 122 is activated again and starts discharging the liquid 130 from the liquid tank 109. A liquid level gauge 119, which constantly monitors the level of the liquid 130, causes the conveying pump 122 to stop when the level of the liquid 130 becomes slightly lower than that of the surface of the wafer chuck 112. Therefore, the amount of the liquid 130 discharged from the liquid tank 109 is small. After that, a vacuum of the wafer chuck 112 is turned off. Then, the wafer 102 on the wafer chuck 112 is moved with a conveying hand 111-4 and stored in the wafer cassette 110. At a point immediately before the storage of the wafer 102 in the wafer cassette 110, the liquid 130 may be removed from the wafer 102 by blowing clean air onto both surfaces of the wafer 102.

As illustrated in FIG. 9B, Japanese Patent Laid-Open No. 6-124873 also discloses a structure in which only part including the wafer chuck 112 is disposed in the liquid tank 109. A structure in which the wafer chuck 112 is directly disposed on the bottom surface of the liquid tank 109, which is disposed on the fine-motion stage 114, is also disclosed. That is, Japanese Patent Laid-Open No. 6-124873 disposes the exposure apparatus in which the last surface of the projection optical system 104 and the entire wafer 102 are disposed in the liquid tank 109.

International Patent Publication No. WO99/049504 describes another example in which the liquid immersion method is applied to an exposure apparatus. International Patent Publication WO99/049504 discloses an exposure apparatus in which a liquid is supplied exclusively to the space between a projection optical system and a wafer surface such that the space is filled with the liquid.

FIG. 10 illustrates an inline connection between an exposure apparatus 153 and a coating/developing device 152 disclosed in Japanese Patent Laid-Open No. 2002-057100. Upon receipt of a wafer from the coating/developing device 152, a wafer conveying robot of the exposure apparatus 153 conveys the wafer to a wafer stage (exposure stage) 155. The same wafer conveying robot also conveys the exposed wafer to the coating/developing device 152. In the coating/developing device 152, a robot which conveys a wafer coated with a resist to an interface 154 adjacent to the exposure apparatus 153 conveys the exposed wafer to a heating unit.

In the conventional exposure apparatuses described above, even if a liquid between the projection optical system and the wafer surface is discharged to the outside after exposure, some liquid may remain on the last surface of a projection lens. This means that the liquid adhering to the last surface of the projection lens may be dropped onto the wafer during handling of the wafer. Moreover, the liquid on the wafer may further be dropped onto the wafer chuck during conveyance of the wafer, cause local defocusing, and lead to lower yields. Additionally, this requires replacement of the wafer chuck, involves a considerable amount of apparatus downtime associated with the replacement, and thus significantly affects the device productivity. Moreover, if the liquid adheres to the conveying hand during conveyance of an exposed and wet wafer, the liquid further adheres to an unexposed wafer to be subsequently conveyed. In other words, cross-contamination occurs. This causes local defocusing and leads to lower yields.

Furthermore, if a wafer to which a liquid adheres is conveyed to the coating/developing device and subjected to heat treatment, heat of evaporation of the liquid causes temperature non-uniformity and degradation in critical dimension (CD) uniformity. If high-speed spin drying or the like is performed under assumption that all exposed wafers are wet, the structure of the exposure apparatus is made complex. This causes an increase in cost and a reduction in throughput.

SUMMARY OF THE INVENTION

The present invention has been made in view of the background descried above and provides a technique for detecting droplets on a substrate in an exposure apparatus to which the liquid immersion method is applied.

According to an aspect of the present invention, an exposure apparatus includes a projection optical system configured to project light from an original, wherein the exposure apparatus exposes a substrate to light through liquid filling a gap between the projection optical system and the substrate, the projection optical system, and the original; and a detecting device configured to detect a droplet adhering to the exposed substrate. The detecting device includes a storage unit configured to prestore first image data corresponding to the unexposed substrate and an image-capturing unit configured to capture an image of a surface of the exposed substrate. The detecting device detects the droplet on the basis of a comparison between the first image data and second image data obtained by the image-capturing unit.

According to another aspect of the present invention, an exposure apparatus includes a projection optical system configured to project light from an original, wherein the exposure apparatus exposes a substrate to light through liquid filling a gap between the projection optical system and the substrate, the projection optical system, and the original; and a detecting device configured to detect a droplet adhering to the exposed substrate. The detecting device includes an irradiating unit configured to irradiate a space along a surface of the substrate with light, a light detecting unit configured to detect light from the droplet, and a smoothing unit configured to smooth image data obtained by the light detecting unit. The detecting device detects the droplet on the basis of the image data obtained by the smoothing unit.

According to another aspect of the present invention, an exposure apparatus includes a projection optical system configured to project light from an original, wherein the exposure apparatus exposes a substrate to light through liquid filling a gap between the projection optical system and the substrate, the projection optical system, and the original; and a detecting device configured to detect a droplet adhering to the exposed substrate. The detecting device includes an irradiating unit configured to irradiate a surface of the substrate with light, a first light detecting unit configured to detect P-polarized light from the surface irradiated with light, and a second light detecting unit configured to detect S-polarized light from the surface irradiated with light. The detecting device detects the droplet on the basis of a comparison between image data obtained by the first light detecting unit and image data obtained by the second light detecting unit.

According to another aspect of the present invention, an exposure apparatus includes a projection optical system configured to project light from an original, wherein the exposure apparatus exposes a substrate to light through liquid filling a gap between the projection optical system and the substrate, the projection optical system, and the original; and a detecting device configured to detect a droplet adhering to the exposed substrate. The detecting device includes an irradiating unit configured to irradiate a surface of the substrate with infrared light and a Fourier transform infrared spectrophotometer configured to detect light from the surface irradiated with infrared light. The detecting device detects the droplet on the basis of a spectrum obtained by the Fourier transform infrared spectrophotometer.

According to another aspect of the present invention, a method of manufacturing a device includes the steps of exposing a substrate to light using one of the exposure apparatuses defined above, developing the exposed substrate, and processing the developed substrate to manufacture the device.

Other features and advantages besides those discussed above shall be apparent to those skilled in the art from the description of several preferred embodiments of the invention which follows. In the description, reference is made to accompanying drawings, which form apart thereof, and which illustrate an example of the invention. Such example, however, is not exhaustive of the various embodiments of the invention, and therefore reference is made to the claims which follow the description for determining the scope of the invention.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 1A schematically illustrates an example structure of a liquid immersion type exposure apparatus according to an exemplary embodiment of the present invention; while

FIG. 10 illustrates an inline connection between a conventional exposure apparatus and coating/developing device.

DESCRIPTION OF THE EMBODIMENTS

The present invention is effective for any exposure apparatuses to which a liquid immersion method using e.g., ultraviolet light as exposure light and filling a space between a projection optical system and a substrate (e.g., wafer) with a liquid is applied. Some examples of such exposure apparatuses may include an exposure apparatus which projects and transfers an original pattern onto a stationary substrate, and an exposure apparatus which forms by scanning exposure a pattern of an original on a substrate using slit light while synchronously scanning the substrate and the original.

First Exemplary Embodiment

Figure 1A:
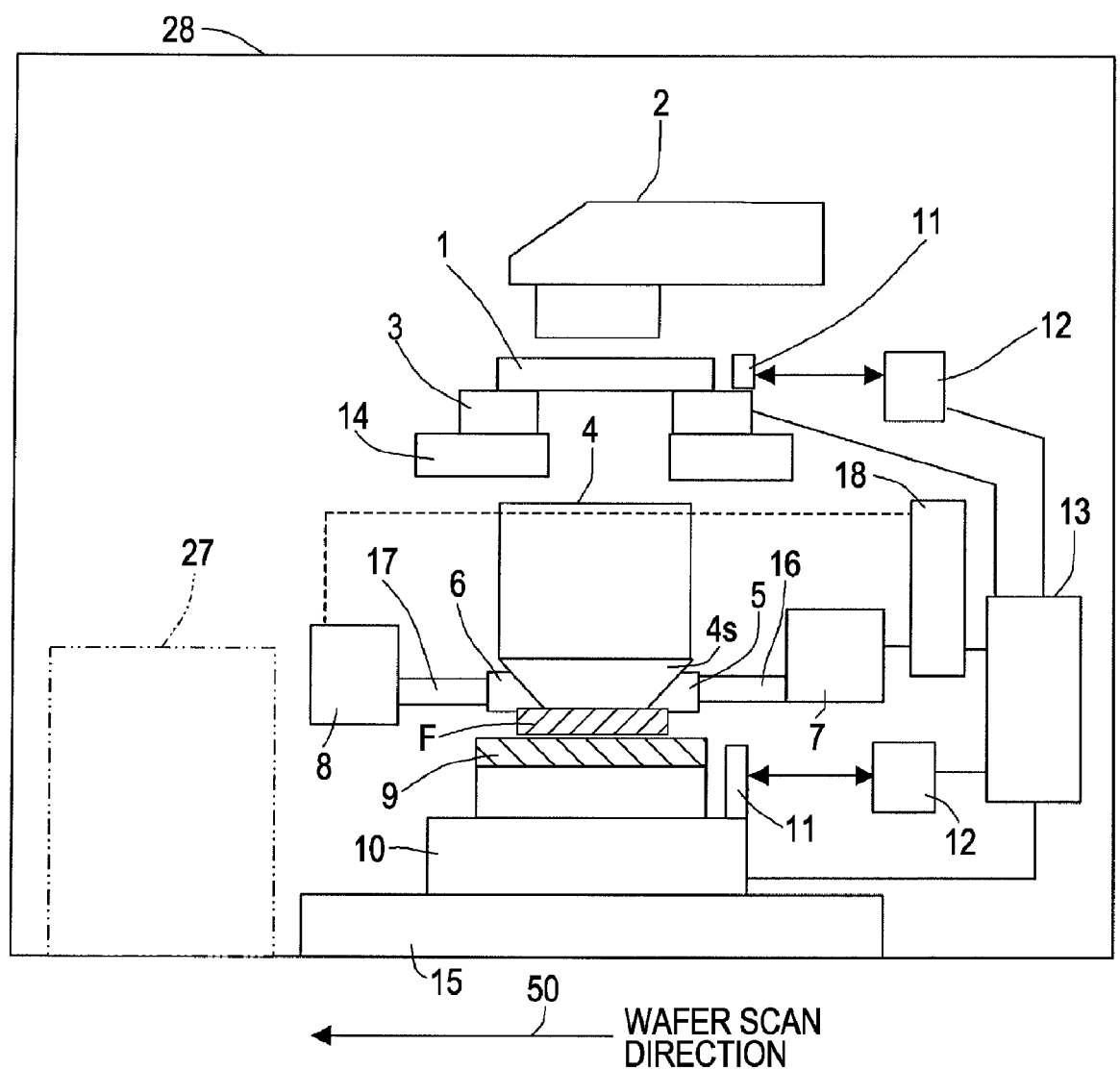
Figure 1B:
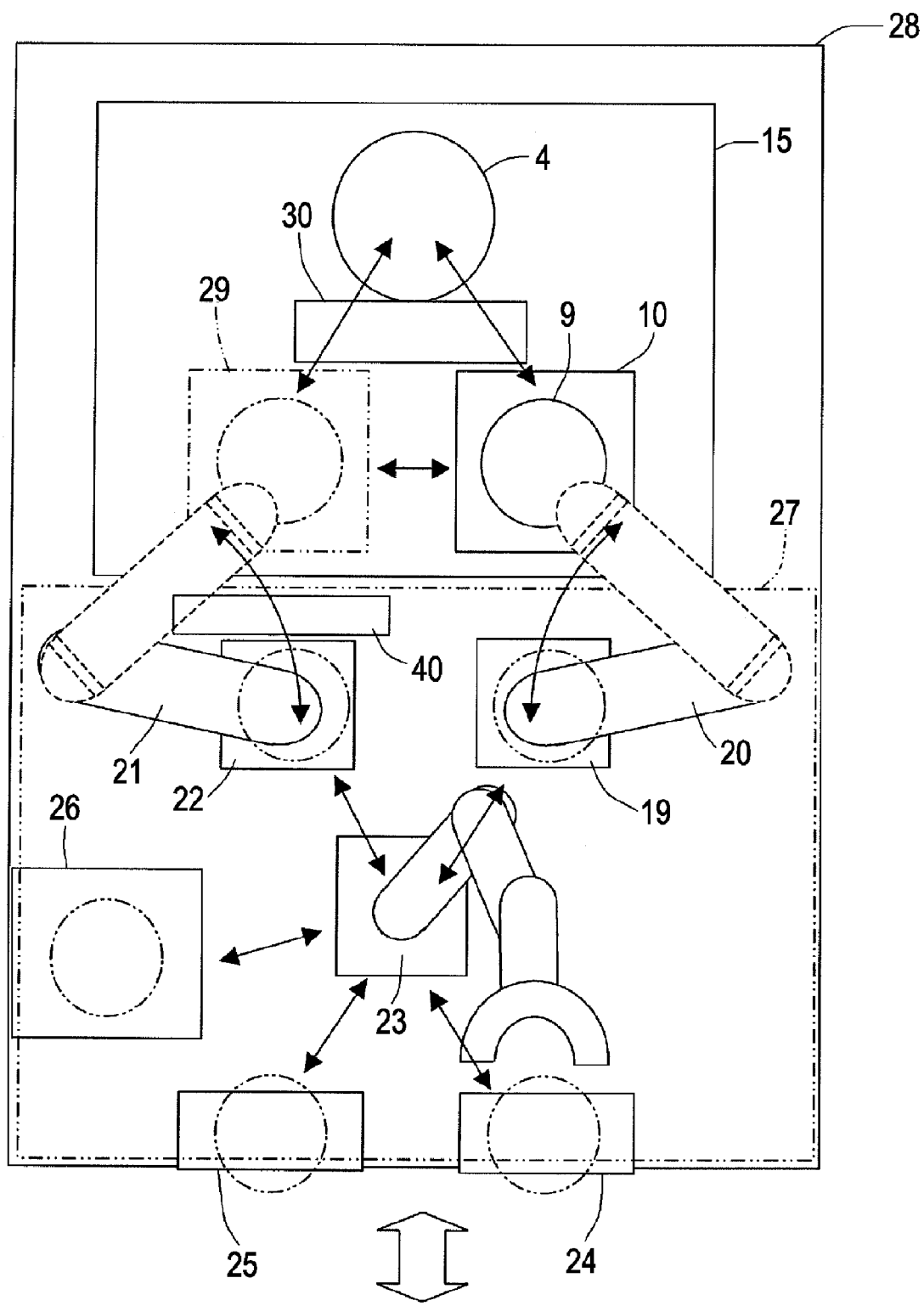
FIG. 1B is a top view showing a cross section of the exposure apparatus of FIG. 1A taken at a wafer conveying level, and schematically illustrates a wafer conveying process.

Exemplary embodiments of the present invention will now be described. FIG. 1A and FIG. 1B schematically illustrate a structure of a liquid immersion type exposure apparatus according to a first exemplary embodiment of the present invention. Referring to FIG. 1A, light emitted from an exposure light source (not shown), such as an ArF excimer laser or an $F_2$ laser, is supplied to an illumination optical system 2. The illumination optical system 2 uses the light supplied from the exposure light source to illuminate part of a reticle (original) 1 with slit light having a slit-shaped cross section. While the illumination optical system 2 is illuminating the reticle 1 with the slit light, a reticle stage (original stage) 3 holding the reticle 1 and a wafer stage (substrate stage) 10 holding a wafer (substrate) 9 move, for scanning, in synchronization with each other. This synchronous scanning enables an image of the entire pattern on the reticle 1 to be continuously formed on the wafer 9 through a projection optical system 4 and causes a resist on the surface of the wafer 9 to be exposed. The reticle stage 3 and the wafer stage 10 are placed on a base 14 and a base 15, respectively.

A reference mirror 11 and a laser interferometer 12 measure the two-dimensional positions of the reticle stage 3 and wafer stage 10 in real time. On the basis of these measurements, a stage controller 13 performs positioning and synchronous control of the reticle 1 (or reticle stage 3) and wafer 9 (or wafer stage 10). The wafer stage 10 includes a driving unit which adjusts, changes, or controls the vertical position, rotational direction, and inclination of the wafer 9. During exposure, the driving unit controls the wafer stage 10 such that an exposure area on the wafer 9 consistently and precisely coincides with the focal plane of the projection optical system 4. The position (vertical position and inclination) of the upper surface of the wafer 9 is measured by an optical focus sensor (not shown) and is supplied to the stage control apparatus 13.

A main body of the exposure apparatus is placed in an environment chamber 28, which allows the ambient temperature surrounding the main body of the exposure apparatus to be maintained at a predetermined temperature. Additionally, individually temperature-controlled air for air conditioning is blown separately to a space surrounding the reticle stage 3, wafer stage 10, and laser interferometer 12, and to a space surrounding the projection optical system 4. Therefore, the ambient temperature is maintained with higher accuracy. A wafer conveying device 27 is placed in front of the main body of the exposure apparatus.

A wafer conveying process will now be described with reference to FIG. 1A and FIG. 1B. FIG. 1B is a top view showing a cross section of the exposure apparatus of FIG. 1A taken at a wafer conveying level, and schematically illustrates a wafer conveying process.

First, a conveying robot 23 conveys, to a pre-alignment unit 19, a wafer placed at a transfer position 24 by a wafer conveying unit (not shown) of a coating/developing apparatus. After the wafer is placed on the pre-alignment unit 19, horizontal and rotational positioning of the wafer is performed. Next, a supply robot 20 conveys the wafer from the pre-alignment unit 19 to the wafer stage 10. While being held by the wafer stage 10, the wafer 9 is moved to an exposure start position under the projection optical system 4. In the vicinity of the exposure start position, a liquid is supplied from a liquid supply nozzle 5 onto the wafer 9. Then, exposure is performed by the liquid immersion method described above.

After completion of the exposure, the liquid on the wafer 9 is recovered through a liquid recovery nozzle 6. While being held by the wafer stage 10, the wafer 9 is moved from under the liquid recovery nozzle 6 to a wafer recovery position 29. To detect, on a conveyance path from under the liquid recovery nozzle 6 to a wafer recovery station 22, droplets that may adhere to the surface of the wafer 9, a droplet detector 30 is disposed on a wafer stage path along which the wafer stage 10 moves. If no droplet is detected on the wafer 9 when the wafer 9 reaches the wafer recovery position 29, the wafer 9 at the wafer recovery position 29 is conveyed by a recovery robot 21 to the wafer recovery station 22. An air knife 40 is disposed on a wafer conveyance path along which the wafer 9 is conveyed from the wafer recovery position 29 to the wafer recovery station 22. If a droplet is detected on the wafer 9 when the wafer 9 reaches the wafer recovery position 29, the air knife 40 removes the droplet from the wafer 9. The conveying robot 23 conveys the wafer 9 from the wafer recovery station 22 to the transfer position 25. The wafer conveying unit (not shown) of the coating/developing apparatus conveys the wafer 9 from the transfer position 25 to the coating/developing apparatus.

Instead of being supplied a wafer from the coating/developing apparatus, the conveying robot 23 may take out an unexposed wafer from a wafer carrier unit 26 in the environment chamber 28, convey it to the pre-alignment unit 19, convey an exposed wafer from the wafer recovery station 22, and store it in the wafer carrier unit 26. In either case, the conveying robot 23 conveys both an unexposed wafer and an exposed wafer.

The present exemplary embodiment adopts the liquid immersion method in which a space or gap between the projection optical system 4 and the wafer 9 is filled with a liquid. This liquid immersion method is realized by the liquid supply nozzle 5 disposed above the wafer 9 and near the projection optical system 4 and also by the liquid recovery nozzle 6 disposed opposite the liquid supply nozzle 5 with the projection optical system 4 interposed therebetween.

The liquid immersion method performed in the present exemplary embodiment will now be described in detail. The liquid supply nozzle 5 is disposed near the projection optical system 4 and on the upstream side in a wafer scan direction in which the exposure apparatus scans the wafer 9 during exposure. For example, when the wafer 9 is moved from right to left, that is, in a second direction, the upstream side in the wafer scan direction is the right side in a first direction that is opposite the second direction. In other words, when the wafer scan direction (second direction) is indicated by an arrow 50, the direction (first direction) toward the starting point of the arrow 50 is the direction toward the upstream side in the wafer scan direction. The liquid recovery nozzle 6 is disposed opposite the liquid supply nozzle 5 (i.e., on the downstream side in the wafer scan direction) with the projection optical system 4 interposed therebetween.

The liquid supply nozzle 5 is connected through a supply pipe 16 to a liquid supply device 7. Similarly, the liquid recovery nozzle 6 is connected through a recovery pipe 17 to a liquid recovery device 8. The liquid supply device 7 may include, for example, a tank for storing liquid, a pumping unit for feeding liquid, a flow controller for controlling the flow rate of liquid to be supplied, and preferably a temperature controller for controlling the temperature of liquid to be supplied. The liquid recovery device 8 may include, for example, a tank for temporarily storing recovered liquid, a suction unit for sucking liquid, and a flow controller for controlling the flow rate of liquid to be recovered. A liquid immersion controller 18 receives information, for example, about the current position, speed, acceleration, target position, and moving direction of the wafer stage 10. On the basis of such information, the liquid immersion controller 18 provides the liquid supply device 7 or liquid recovery device 8 with an instruction to start or stop immersion or to control the flow rate of liquid.

A process for filling a space between the projection optical system 4 and the wafer 9 with a liquid will now be described. First, while the wafer 9 is at rest or in motion, a liquid F is supplied from the liquid supply nozzle 5 onto the wafer 9, for example, at a substantially constant flow rate. A sufficient liquid film can be formed by bringing the liquid F into tight contact with both the lower surface of the liquid supply nozzle 5 and the upper surface of the wafer 9. While the liquid F is being supplied from the liquid supply nozzle 5, the wafer 9 starts moving without breaking the formed liquid film. When the wafer 9 reaches an exposure starting position, scanning exposure using slit light starts. When the wafer 9 further moves to reach an exposure ending position, exposure using slit light ends. Upon completion of the exposure using slit light, the supply of the liquid F from the liquid supply nozzle 5 is stopped. While the wafer 9 is being moved in the wafer scan direction, the residual liquid is recovered through the liquid recovery nozzle 6. As described above, the liquid F is continuously supplied from the liquid supply nozzle 5 onto the surface of the wafer 9 while the wafer 9 is being moved so that a liquid film spreads as the wafer 9 moves. This allows a gap between the last surface 4s of the projection optical system 4 and the wafer 9 to be filled with a continuous liquid film (unbroken liquid film). Also, since the spreading speed of the liquid film relative to the moving speed of the wafer 9 is small, the residual liquid can be reliably recovered through the liquid recovery nozzle 6.

Normally, the foregoing liquid supply/recovery method allows recovery of all droplets on an exposed wafer. However, it is possible that some droplets adhering to the liquid recovery nozzle 6 or the last surface 4s of the projection optical system 4 are dropped onto the wafer. Moreover, although it is unlikely to occur, the droplets dropped onto the wafer may further be dropped onto a wafer chuck during conveyance of the wafer, cause local defocusing, and lead to lower yields. Additionally, this requires replacement of the wafer chuck, involves a considerable amount of apparatus downtime associated with the replacement, and thus significantly affects the device productivity. Moreover, if the liquid adheres to the hand of the conveying robot 23 during conveyance of an exposed and wet wafer, the liquid further adheres to an unexposed wafer to be subsequently conveyed. In other words, cross-contamination occurs. This causes local defocusing and leads to lower yields.

Furthermore, if a wafer to which the liquid adheres is conveyed to the coating/developing apparatus and subjected to heat treatment, a process problem occurs in that heat of evaporation of the liquid causes temperature non-uniformity and degradation in CD uniformity. If high-speed spin drying or the like is performed under assumption that all exposed wafers are wet, the structure of the exposure apparatus is made complex. This causes an increase in cost and a reduction in throughput. Therefore, it is necessary to detect droplets on a wafer and dry the wafer in a manner appropriate for the detected droplets. The exposure apparatus of the present exemplary embodiment provides a droplet detector capable of detecting droplets on a wafer and a droplet remover capable of removing the detected droplets from the wafer.

Figure 2:
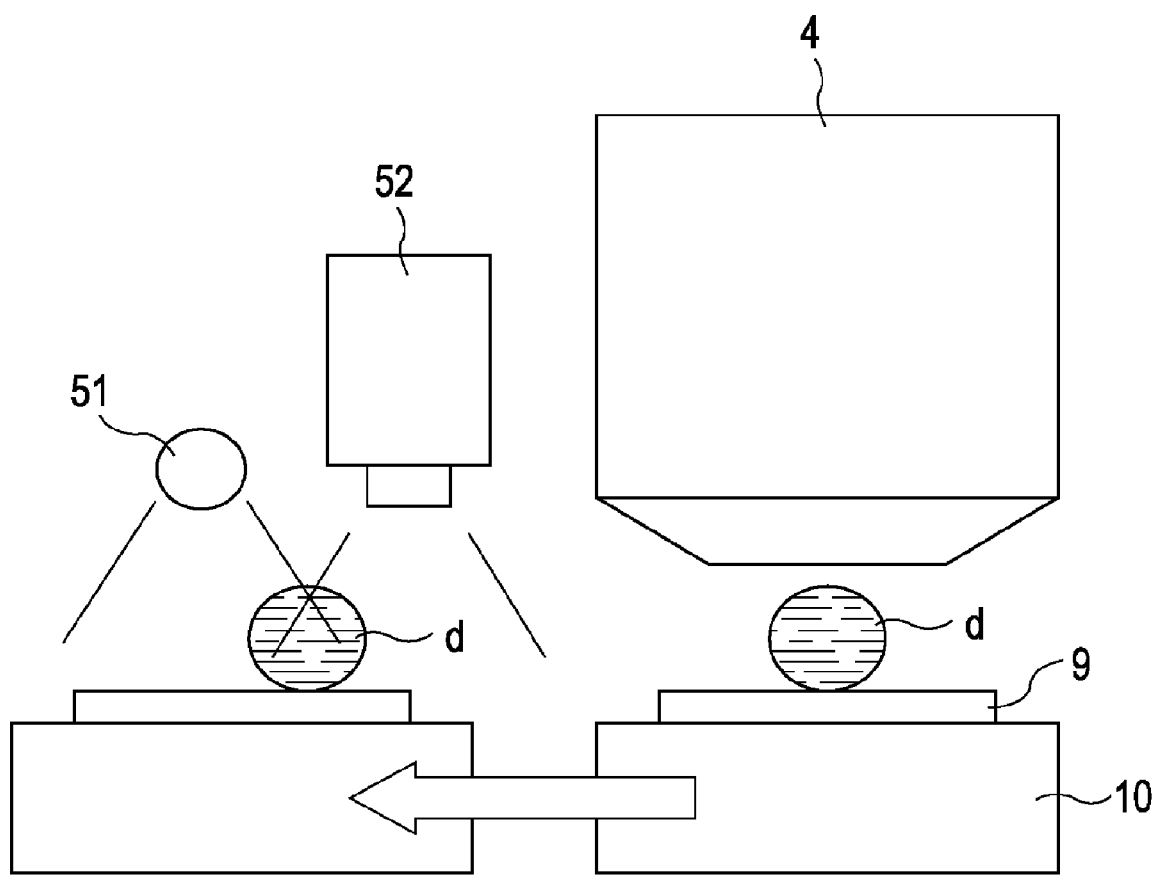
FIG. 2 is a schematic view illustrating a droplet detector which detects droplets on a wafer according to a first exemplary embodiment of the present invention.

FIG. 2 is a schematic view illustrating the droplet detector (detecting device) 30 which detects droplets on the wafer 9 according to the present exemplary embodiment. The droplet detector 30 includes an illuminating unit (irradiating unit) 51 which emits light and a light detecting unit 52 which detects light. An infrared light source is used as the illuminating unit 51, and a charge-coupled device (CCD) sensor camera is used as the light detecting unit 52. Besides the infrared light source, a light source having a wavelength not causing a resist to be exposed can be used as the illuminating unit 51. Examples of the illuminating unit 51 include a laser beam source, laser sheet beam source, laser scan beam source, light-emitting diode (LED), and light bulb with a yellow filter. As the light detecting unit 52, a light detecting element that is sensitive to the wavelength of the illuminating unit 51 can be used. Examples of the light detecting unit 52 include a two-dimensional sensor such as a CCD sensor or complementary metal-oxide semiconductor (CMOS), a one-dimensional sensor such as a line sensor, and a photoelectric sensor. The illuminating unit 51 emits flashes of infrared light to the wafer 9 that has been subjected to liquid immersion exposure and is being moved from under the liquid recovery nozzle 6 to the wafer recovery position 29 while being held by the wafer stage 10. Thus, the CCD sensor camera can capture an image of the wafer 9 and a droplet "d" thereon. In the present exemplary embodiment, the CCD sensor camera has a field of view which allows capturing of an image of the entire surface of the wafer stage 10. Even if the CCD sensor camera has a narrower field of view or cannot observe the entire surface of the wafer 9 due to the presence of the projection lens or the like, the entire image of the wafer 9 can be captured in segments by continuously photographing the wafer 9 as the wafer stage 10 moves. This allows detection of droplets on the entire surface of the wafer 9. A similar effect can be achieved by capturing the entire image of the wafer 9 in segments while varying the orientation of the CCD sensor camera and putting the segments together later by image processing. Even when a one-dimensional sensor (such as a line sensor), instead of a two-dimensional sensor (such as a CCD sensor or CMOS), is used as the light detecting unit 52, it is possible to detect droplets on the entire surface of the wafer 9 by controlling the movement of the wafer stage 10 or the orientation of the light detecting unit 52 to allow relative movement of the wafer 9 and the CCD sensor camera.

In the semiconductor device manufacturing process, a device is formed by stacking different layers on the surface of a wafer. Therefore, in a wafer conveyed to the exposure apparatus, a device pattern on a predetermined layer is typically coated with a thin resist film having a thickness of about 1 μm. In a wafer image captured by the CCD sensor camera, a device pattern visible through a thin resist film and foreign matter adhering to the surface of the wafer, as well as droplets, will be observed. This means that it is necessary to discriminate droplets from the device pattern and foreign matter on the wafer. In the present exemplary embodiment, an image captured by the CCD sensor camera is processed by a droplet discriminating unit in a controller (not shown). Thus, droplets can be discriminated from a device pattern or foreign matter on the wafer.

There will now be described an example discriminating unit which discriminates, in an image captured by the CCD sensor camera, droplets from a device pattern on a wafer.

Figure 3:
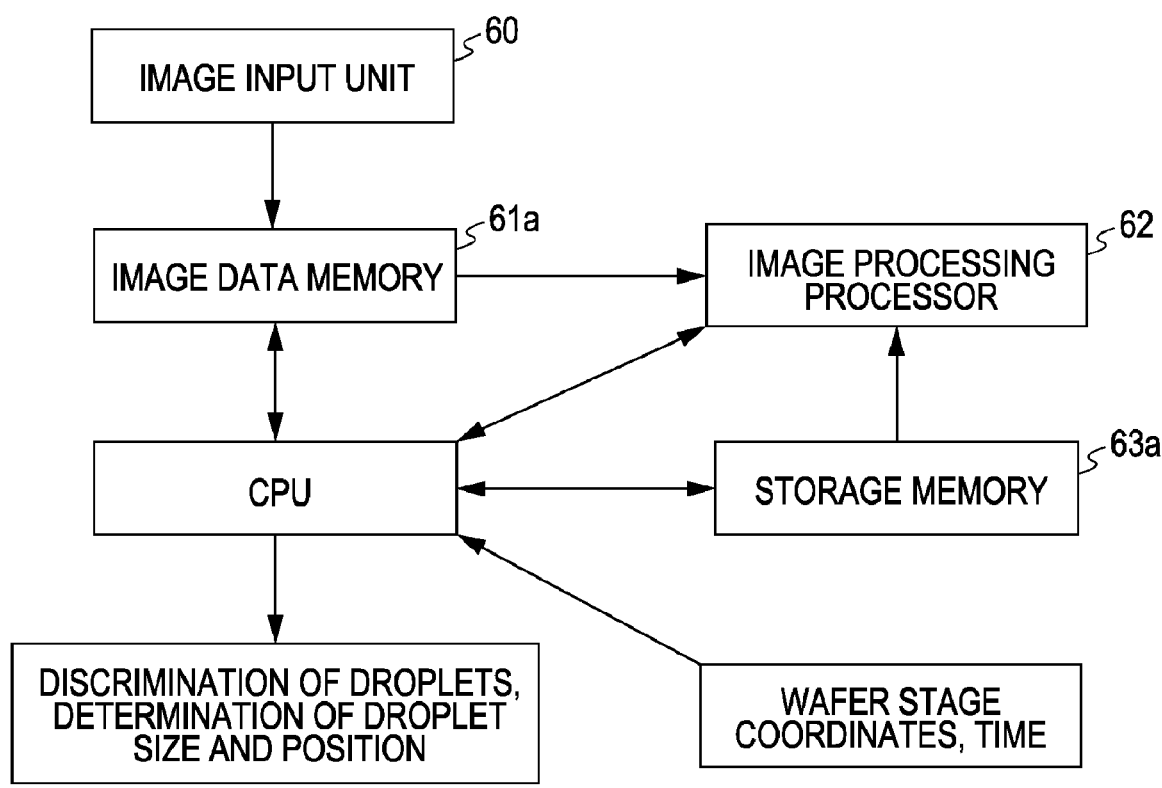
FIG. 3 is a block diagram illustrating a discriminating unit which discriminates droplets from a device pattern on a wafer according to the first exemplary embodiment.

FIG. 3 is a block diagram illustrating a discriminating unit which discriminates droplets from a device pattern on a wafer according to the present exemplary embodiment. Image data captured by the light detecting unit 52 (i.e., CCD sensor camera) serving as an image input unit 60 is stored in an image data memory 61a. An image processing processor 62 compares this image data with image data prestored in a storage memory 63a to identify droplets on the wafer. The image data prestored in the storage memory 63a is image data that should be captured by the CCD sensor camera if no droplet is present on the surface of the wafer. For example, the image data prestored in the storage memory 63a may either be image data obtained by actually photographing the wafer by the CCD sensor camera or image data generated on the basis of data representing a device pattern formed on the wafer. Various techniques known to those skilled in the art are applicable to the comparison described above. For example, various types of inter-image operation (calculation) for calculating a difference or correlation between images and extracting regions that are different between images are applicable to the comparison. In addition to identifying droplets on the wafer, the position and size of the droplets are determined on the basis of information about coordinates of the wafer stage 10. According to the resulting information about the position and size of the droplets, the controller (now shown) controls a droplet remover. If it is detected that there is no droplet on the wafer, the controller (now shown) performs control such that a droplet removal process is not performed.

In the present exemplary embodiment, pure water is used as a liquid immersion fluid for liquid immersion exposure. This means that droplets to be detected and removed are pure water droplets. However, a liquid immersion fluid for the liquid immersion exposure is not limited to pure water. Droplets can be similarly detected and removed even if a liquid immersion fluid such as perfluoropolyether (e.g., Fomblin) is used.

Also in the present exemplary embodiment, the droplet detector 30 for detecting droplets on the wafer 9 is disposed on the wafer stage path along which the wafer stage 10 moves. However, the droplet detector may be disposed at any position on a wafer conveyance path from the wafer stage path to the transfer position 25. Similar effects can be obtained even if the droplet detector is disposed, for example, above the wafer recovery position 29, wafer recovery station 22, conveying robot 23, or transfer position 25.

Additionally, in the present exemplary embodiment, the air knife 40 serving as a droplet remover is disposed on the wafer conveyance path along which the wafer 9 is conveyed from the wafer recovery position 29 to the wafer recovery station 22. However, the droplet remover may be disposed at any position on the wafer conveyance path from the wafer stage path to the transfer position 25. Similar effects can be obtained even if the droplet remover is disposed, for example, above the wafer recovery position 29, wafer recovery station 22, conveying robot 23, or transfer position 25. As an alternative to the air knife 40, a liquid immersion nozzle (e.g., liquid recovery nozzle 6) may be used to remove droplets.

Second Exemplary Embodiment

A structure of a liquid immersion type exposure apparatus according to a second exemplary embodiment of the present invention is basically the same as that of the first exemplary embodiment. Hereinafter, a wafer conveying process of the second exemplary embodiment will be described with reference to FIG. 1B. First, the conveying robot 23 conveys, to the pre-alignment unit 19, a wafer placed at the transfer position 24 by the wafer conveying unit (not shown) of the coating/developing apparatus. After the wafer is placed on the pre-alignment unit 19, horizontal and rotational positioning of the wafer is performed. Next, the supply robot 20 conveys the wafer from the pre-alignment unit 19 to the wafer stage 10. While being held by the wafer stage 10, the wafer 9 is moved to an exposure start position under the projection optical system 4. The droplet detector 30 for detecting droplets on the wafer conveyance path along which the wafer is conveyed from the transfer position 24 or pre-alignment unit 19 to the exposure start position under the projection optical system 4. An image of a device pattern on the surface of the wafer before exposure (before immersion) is captured by a camera in the droplet detector 30 and stored in a first image data memory 63b (see FIG. 4).

Next, in the vicinity of the exposure start position, a liquid is supplied from the liquid supply nozzle 5 (see FIG. 1A) onto the wafer 9. Then, exposure is performed by the liquid immersion method described above. After completion of the exposure, the liquid on the wafer 9 is recovered through the liquid recovery nozzle 6. While being held by the wafer stage 10, the wafer 9 is moved from under the liquid recovery nozzle 6 to the wafer recovery position 29. During the move to the wafer recovery position 29, an image of the surface of the wafer 9 after the exposure (i.e., exposed wafer) is captured by the camera in the droplet detector 30 above the wafer 9 and stored in the first image data memory 63b. The wafer 9 at the wafer recovery position 29 is conveyed by the recovery robot 21 to the wafer recovery station 22. The air knife 40 is disposed on the wafer conveyance path along which the wafer 9 is conveyed from the wafer recovery position 29 to the wafer recovery station 22. The conveying robot 23 conveys the wafer on the wafer recovery station 22 to the transfer position 25. The wafer conveying unit (not shown) of the coating/developing apparatus conveys the wafer at the transfer position 25 to the coating/developing apparatus.

Instead of being supplied a wafer from the coating/developing apparatus, the conveying robot 23 may take out an unexposed wafer from the wafer carrier unit 26 in the environment chamber 28, convey it to the pre-alignment unit 19, convey an exposed wafer from the wafer recovery station 22, and store it in the wafer carrier unit 26. In either case, the conveying robot 23 conveys both an unexposed wafer and an exposed wafer.

Figure 4:
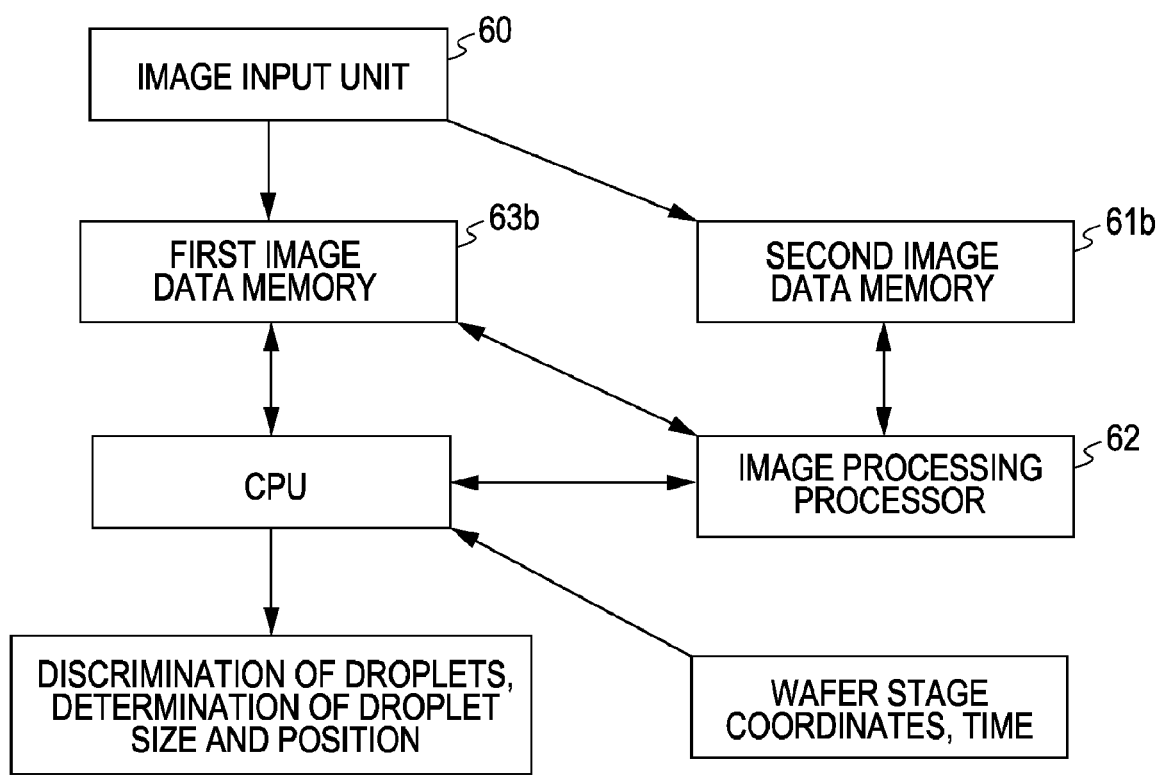
FIG. 4 is a block diagram illustrating a discriminating unit which discriminates droplets from a device pattern on a wafer according to a second exemplary embodiment of the present invention.

FIG. 4 is a block diagram illustrating a discriminating unit which discriminates droplets from a device pattern on a wafer according to the present exemplary embodiment. Image data representing an image of an unexposed wafer captured by a camera serving as the image input unit 60 is stored in the first image data memory 63b. Image data representing an image of an exposed wafer captured in a similar manner is stored in a second image data memory 61b. The image processing processor 62 compares the image data stored in the second image data memory 61b with the image data prestored in the first image data memory 63b to identify droplets on the wafer. At the same time, the position and size of the droplets are determined on the basis of information about coordinates of the wafer stage 10. According to the resulting information about the position and size of the droplets, a controller (now shown) controls a droplet remover. If it is detected that there is no droplet on the wafer, the controller (now shown) performs control such that a droplet removal process is not performed.

Third Exemplary Embodiment

Figure 5:
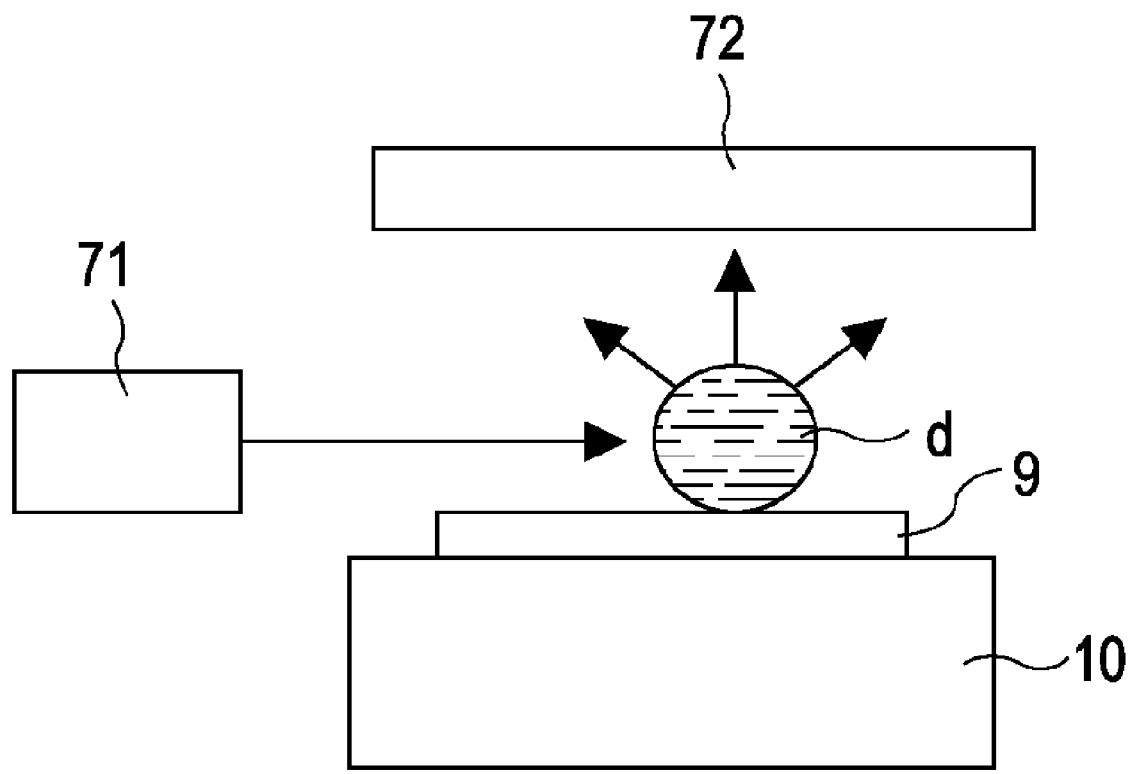
FIG. 5 is a schematic view illustrating a droplet detector which detects droplets on a wafer according to a third exemplary embodiment of the present invention.

FIG. 5 illustrates a droplet detector using a laser 71 as an illuminating unit and a line sensor 72 as a light detecting unit according to a third exemplary embodiment of the present invention. A laser beam emitted from the laser 71 travels parallel to the wafer 9 and near the upper surface of the wafer 9. The line sensor 72 is disposed such that the longer side thereof is parallel to the upper surface of the wafer 9 and to the laser beam. Moving the wafer stage 10 in a direction orthogonal to the longer side of the line sensor 72 allows scanning of the entire surface of the wafer 9. Performing image processing on a signal from the line sensor 72 allows detection of droplets over the entire surface of the wafer 9. If there are droplets on the wafer 9, the line sensor 72 receives laser light scattering off the droplets and thus detects the presence of droplets.

There will now be described a discriminating unit which discriminates, in an image captured by the line sensor 72, droplets from a device pattern or foreign matter on a wafer. The present exemplary embodiment uses a lowpass filter (which may also be referred to as smoothing filter or smoothing unit) as an image processing system to discriminate droplets from a device pattern or foreign matter on a wafer. Typically, inspection devices for detecting foreign matter on a wafer do not use a lowpass filter that passes low frequencies to detect fine particles of foreign matter. The present exemplary embodiment uses, for example, a lowpass filter with a bandwidth of less than or equal to 100 KHz to discriminate droplets with a diameter of about 1 mm from foreign matter particles with a diameter of several tens of µm.

Figure 6A:
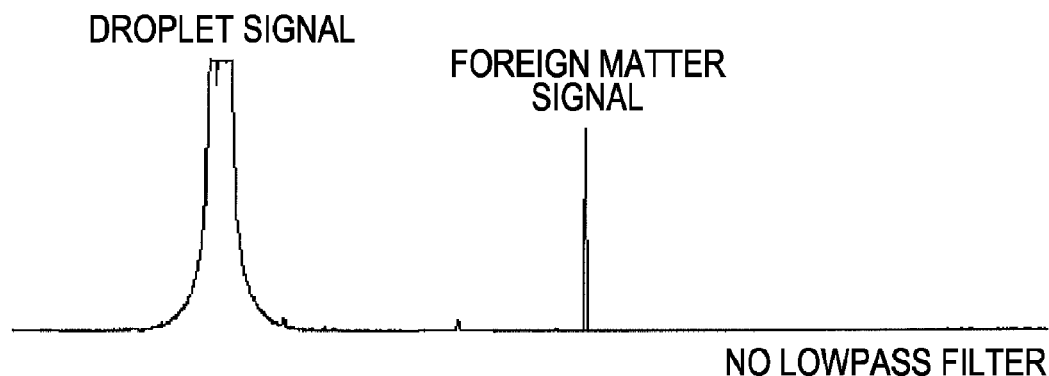
FIG. 6A to FIG. 6C are waveform diagrams each showing droplet and foreign matter signals output from a light detecting unit according to the third exemplary embodiment.
Figure 6B:
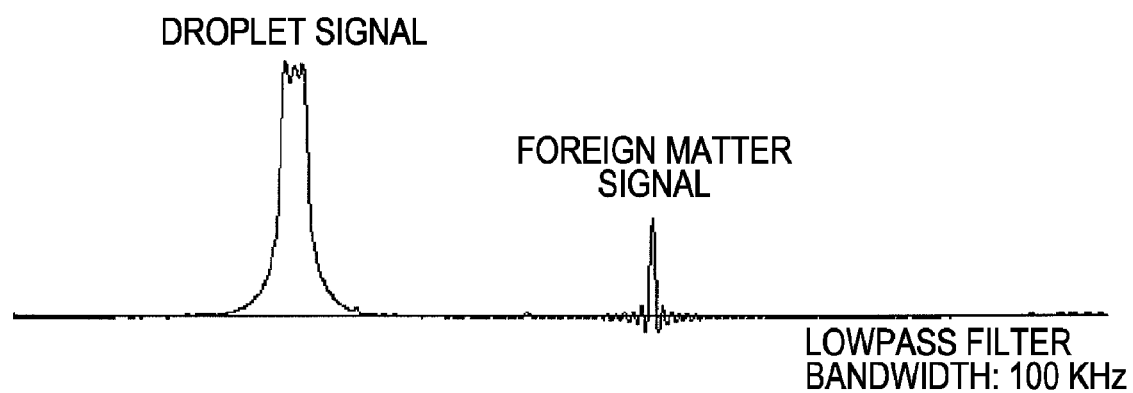
Figure 6C:
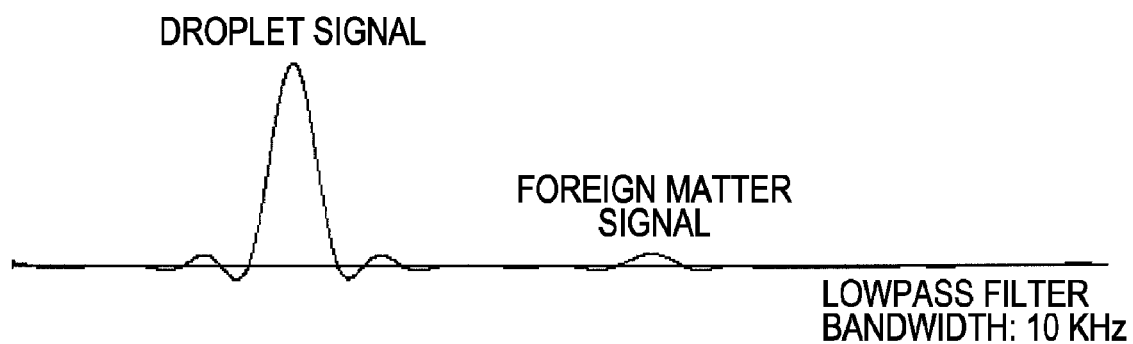

FIG. 6A shows a waveform of droplet and foreign matter signals output from the line sensor 72. The horizontal axis represents the position in the line sensor 72, while the vertical axis represents the strength of output from the line sensor 72. FIG. 6B and FIG. 6C each show a waveform obtained by processing the waveform of FIG. 6A using a lowpass filter. In the waveform of FIG. 6A obtained without using any lowpass filter, the level of the foreign matter signal representing foreign matter on a wafer is high. However, if a lowpass filter with a bandwidth of less than or equal to 100 KHz is used, the level of the foreign matter signal is more greatly attenuated than is the level of the droplet signal as shown in FIG. 6B and FIG. 6C. This allows discrimination between droplets and foreign matter. It is preferable that the bandwidth of the lowpass filter be less than or equal to 100 KHz, and more preferably be less than or equal to 10 KHz. To attenuate the signal level of foreign matter on the wafer, it is preferable to defocus a light detecting unit. The present exemplary embodiment uses an analog lowpass filter to process the output waveform from the line sensor 72. However, to process digital image data obtained by digitizing the output of the line sensor 72, a digital spatial lowpass filter may be used. In this case, an appropriate spatial frequency bandwidth of the spatial lowpass filter may be determined according to the size of droplets and foreign matter particles.

Fourth Exemplary Embodiment

Figure 7:
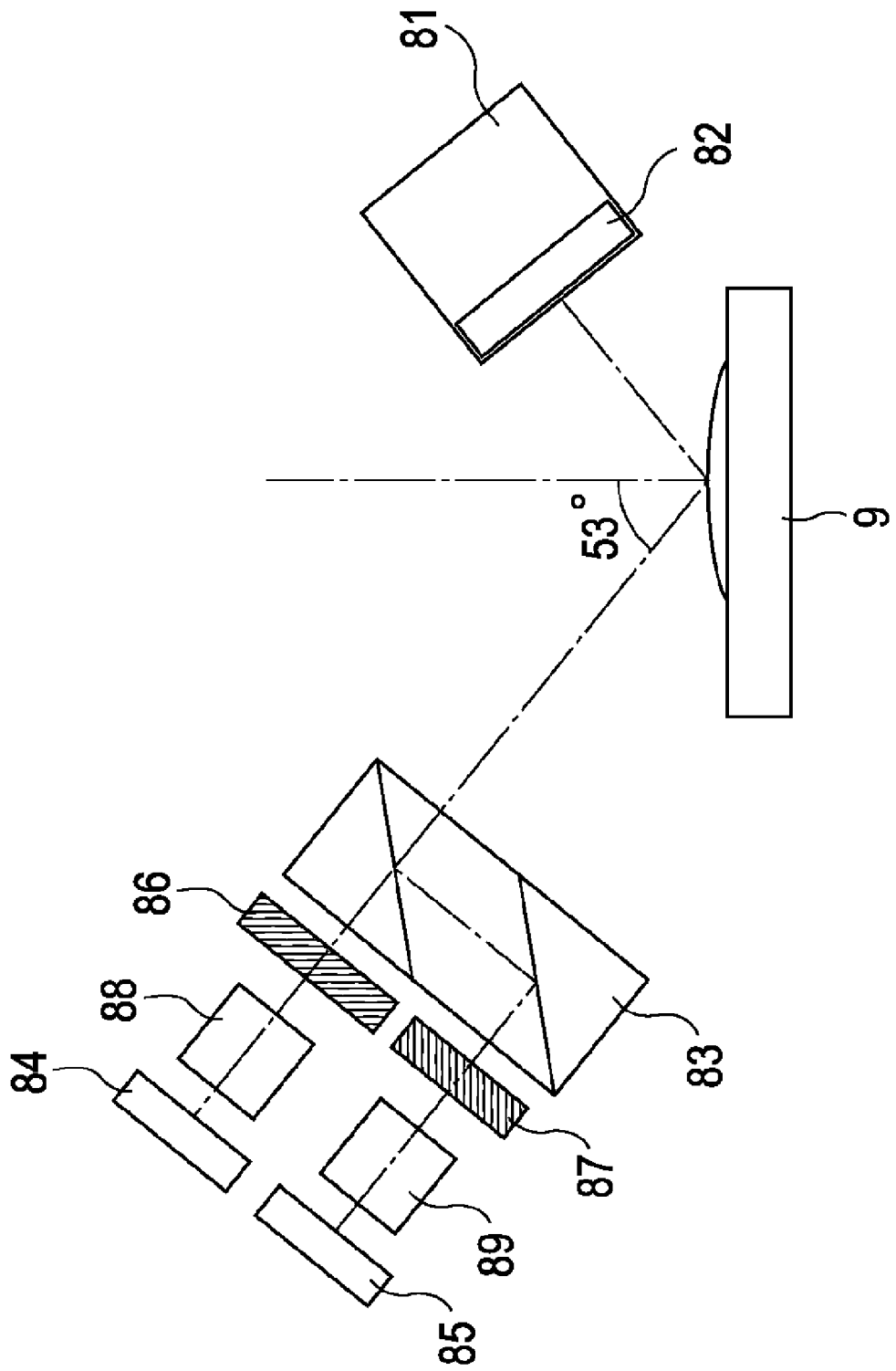
FIG. 7 illustrates a droplet detector using a two-dimensional sensor in a light detecting unit according to a fourth exemplary embodiment of the present invention.

FIG. 7 illustrates an example structure of a droplet detector according to a fourth exemplary embodiment of the present invention. In the droplet detector of FIG. 7, a diffuser 82 is disposed on the light projecting side of an infrared lamp 81 serving as an illuminating unit. This allows the infrared lamp 81 to substantially uniformly illuminate the wafer 9. In a light detecting unit, reflected light from the wafer 9 is split by a splitting optical system 83 into two light beams, which are made incident on respective first and second light detecting elements 84 and 85. Polarizers 86 and 87 and imaging optical systems 88 and 89 which form images of the wafer 9 on the first and second light detecting elements 84 and 85, respectively, are disposed between the splitting optical system 83 and the first and second light detecting elements 84 and 85. The polarizer 86 and polarizer 87 are disposed to allow P-polarized light and S-polarized light to pass therethrough, respectively. The first and second light detecting elements 84 and 85 may be a two-dimensional sensor, such as a CMOS sensor or CCD sensor, or a one-dimensional sensor, such as a line sensor. The first and second light detecting elements 84 and 85 are connected to an image processing unit (not shown).

Figure 8:
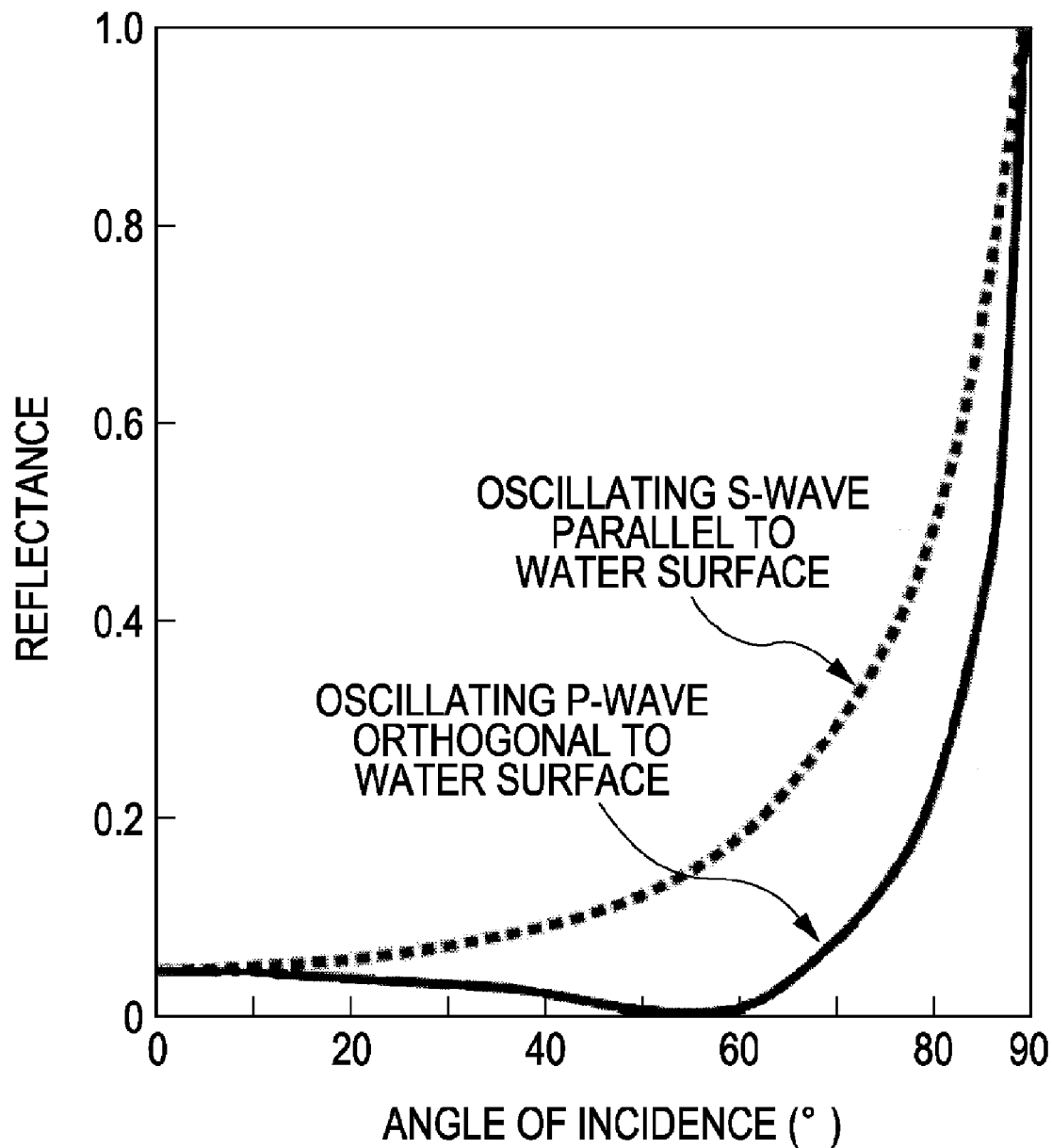
FIG. 8 is a graph showing an exemplary relationship, in the air, between reflectance and the angle of incidence with respect to a water surface.
Figure 9A:
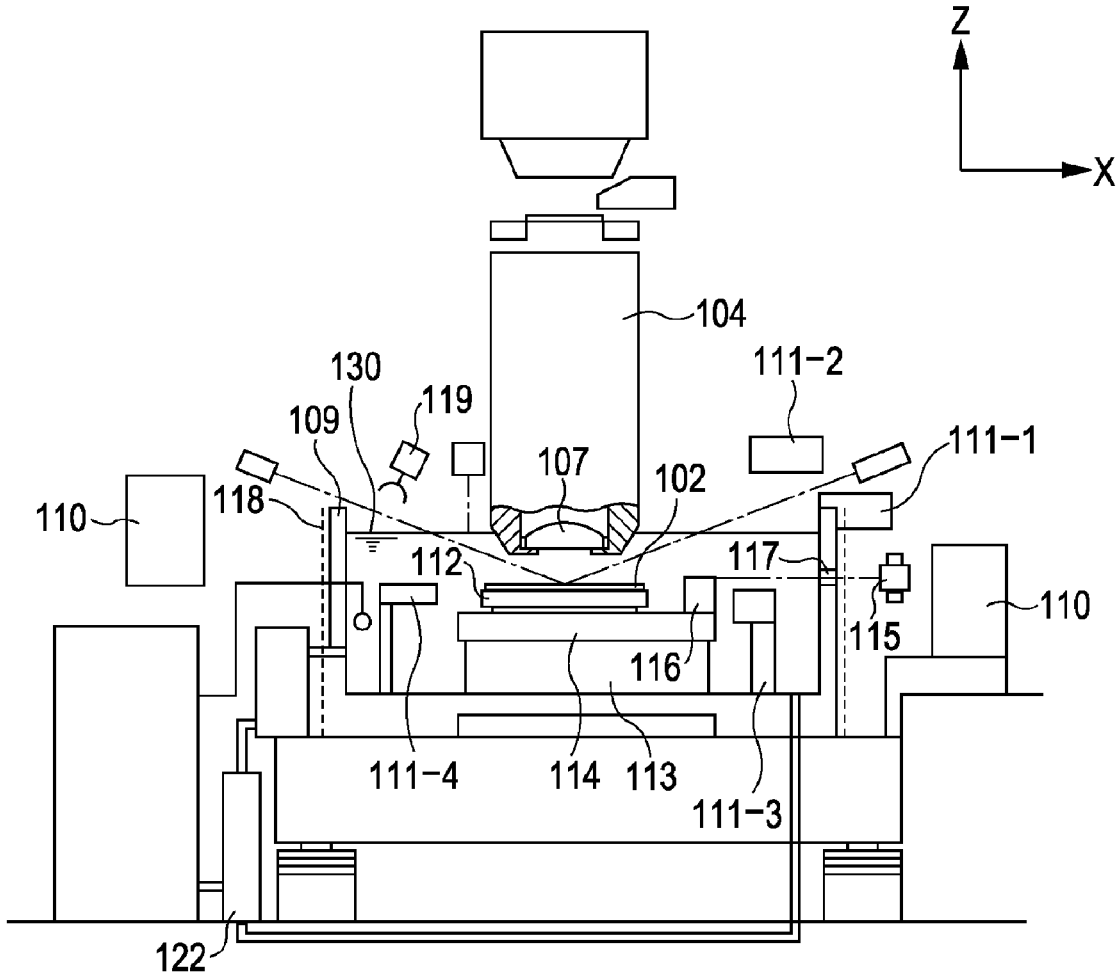
FIG. 9A and FIG. 9B illustrate a conventional liquid immersion type exposure apparatus.
Figure 9B:
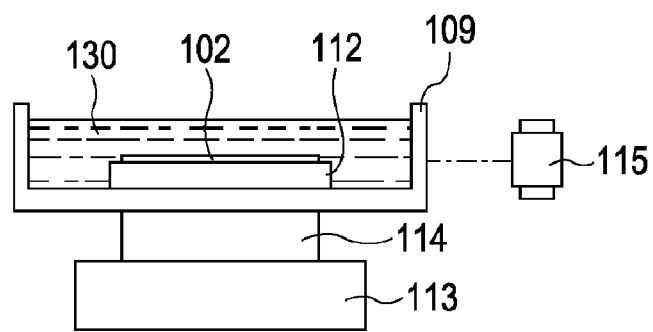

FIG. 8 is a graph showing an exemplary relationship, in the air, between reflectance and the angle of incidence of P-polarized light and S-polarized light with respect to a water surface. The reflectance, while the horizontal axis represents the angle of incidence. The graph shows that P-polarized light and S-polarized light differ in reflectance for the same angle of incidence. A difference in reflectance between P-polarized light and S-polarized light is particularly significant at angles of incidence ranging from 40 to 85 degrees. Therefore, it is preferable to set the optical axes of the respective illuminating unit and light detecting unit at angles in the range of 40 to 85 degrees.

In the present exemplary embodiment, light reflected off the wafer 9 is split by the splitting optical system 83 into two light beams, one forming on the first light detecting element 84 an image deriving only from P-polarized light, the other forming on the second light detecting element 85 an image deriving only from S-polarized light. A comparison between these simultaneously captured images based on P-polarized light and S-polarized light allows identification of water.

The graph of FIG. 8 shows that the reflectance of P-polarized light is lowest when the angle of incidence is 53.1 degrees. This angle is referred to as Brewster's angle. At this angle, virtually no light reflected from water is incident on the first light detecting element 84 which detects P-polarized light only, and light reflected from water is detected only by the second light detecting element 85 which detects S-polarized light only. Therefore, a comparison between signals from the first and second light detecting elements 84 and 85 allows clearer identification of water. It is thus more preferable to set the optical axes of the respective illuminating unit and light detecting unit at angles about 53.1 degrees, that is, about a Brewster's angle.

Even when an immersion exposure fluid (or immersion fluid) other than water, such as perfluoropolyether (e.g., Fomblin), is used, it is still preferable to examine the relationship of the direction of polarization, angle of incidence, and reflectance and select the angle of incidence, angle of reflection, direction of polarization that can create a difference in reflectance. Additionally, for a resist surface on the wafer 9, it is preferable to measure the relationship in the air between reflectance and the angle of incidence of P-polarized light and S-polarized light as in the case of FIG. 8, and select the angle of incidence, angle of reflection, and direction of polarization such that the relationship is distinctly different from that of the immersion liquid.

Fifth Exemplary Embodiment

As a fifth exemplary embodiment of the present invention, there will be described a droplet detector which uses an infrared light source as an illuminating unit, uses a light detecting element sensitive to infrared light as a light detecting unit, and identifies droplets on the basis of a spectrum obtained by the Fourier transform infrared spectroscopy method.

When irradiated with infrared light having different wavelengths (energy levels), molecules absorb infrared light having a specific wavelength corresponding to an energy level that is unique to the molecular vibration and thus, a unique spectrum corresponding to the molecular structure can be obtained. Using such an infrared spectrum makes it possible to estimate a compound structure, quantitate a compound, and identify material on the basis of a comparison with a spectrum of known material. To identify droplets on a wafer, the present exemplary embodiment uses an interferometer in the light detecting unit to detect light, and uses a Fourier transform infrared spectrophotometer (FT-IR) with which data is Fourier-transformed into a spectrum. The present exemplary embodiment has an advantage in that, by comparing with prestored droplet spectrum data to identify droplets, it is possible to clearly discriminate the droplets from a device pattern and foreign material on the wafer.

The above-describe exemplary embodiments make it possible to improve the practicability of an exposure apparatus and exposure method to which the liquid immersion technique is applied. For example, droplets can be detected. Moreover, if droplets are removed only when they are detected, it is possible not only to reduce deterioration in apparatus throughput, but also to reduce the amount of apparatus downtime or deterioration in yield. At the same time, it is possible to reduce possibility of degradation in the performance of a semiconductor manufacturing apparatus or inspection apparatus that processes a wafer conveyed from the exposure apparatus. Additionally, it is possible to make the exposure apparatus smaller or less complex.

The above-describe exemplary embodiments are examples in which the present invention is applied to an exposure apparatus. However, the present invention is also applicable to device manufacturing apparatuses, such as an inspection apparatus for inspecting an immersed and exposed substrate and a resist coating/developing apparatus for processing an exposed substrate. For example, the present invention is effective when applied to a device manufacturing apparatus connected via an inline connection to a liquid immersion type exposure apparatus having a known structure. In this case, if, for example, a conveyance system in the exposure apparatus is divided into a carrying-in system and a carrying-out system, similar effects to those of the above-described exemplary embodiments can be achieved.

Exemplary Embodiment of Microdevice Manufacture

A process of manufacturing, using the liquid immersion type exposure apparatus described above, a microdevice (e.g., a semiconductor chip such as an IC or LSI, liquid crystal panel, CCD sensor, thin-film magnetic head, or micromachine) will now be described.

Figure 11:
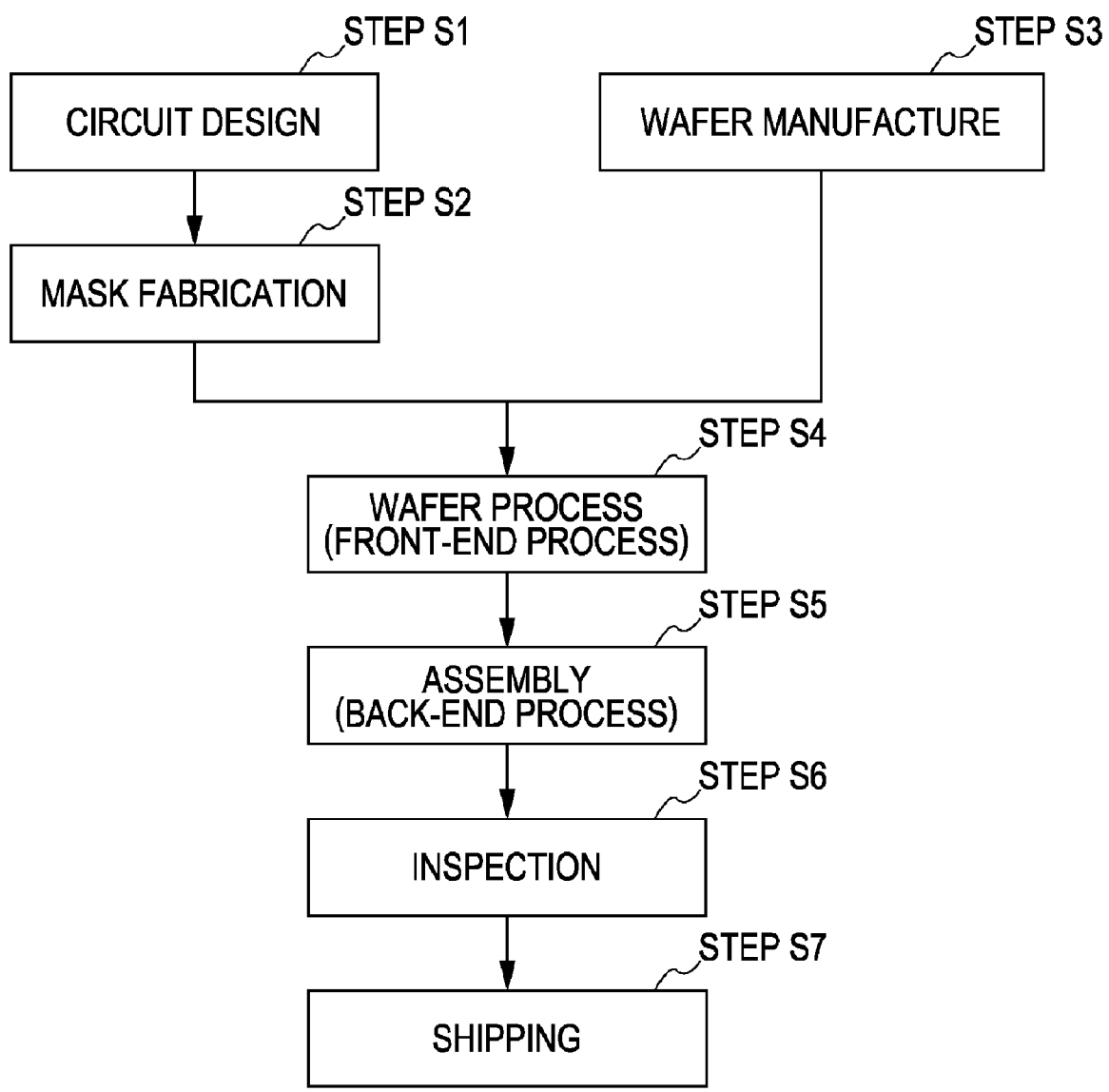
FIG. 11 is an exemplary flow of a device manufacturing process.

FIG. 11 shows an exemplary flow of manufacturing a semiconductor device. In step S1 (circuit design), a semiconductor device circuit is designed. In step S2 (mask fabrication), a mask (also called an original or reticle) on which the designed circuit pattern is formed is fabricated. In step S3 (wafer manufacture), a wafer (also called a substrate) is manufactured from material such as silicon. In step S4 (wafer process), which is referred to as a front-end process, an actual circuit is formed on the wafer by a lithography technique using the wafer and the fabricated mask placed on the exposure apparatus. In step S5 (assembly), which is referred to as a back-end process, a semiconductor chip is formed using the wafer manufactured in step S4. This back-end process includes sub-processes, such as an assembly process (dicing and bonding) and a packaging process (chip encapsulation). In step S6 (inspection), the semiconductor device made in step S5 undergoes inspections, such as an operation check and a durability test. After these steps, the semiconductor device is completed and shipped in step S7 (shipping).

The wafer process of step S4 described above includes an oxidation step, a chemical vapor deposition (CVD) step, an electrode formation step, an ion implantation step, a resist processing step, an exposure step, a development step, an etching step, and a resist removal step. In the oxidation step, the wafer surface is oxidized. In the CVD step, an insulating film is formed on the wafer surface. In the electrode formation step, an electrode is formed on the wafer by vapor deposition. In the ion implantation step, ions are implanted into the wafer. In the resist processing step, a photosensitive agent is applied to the wafer. In the exposure step, the wafer processed in the resist processing step is exposed to light via the mask having the circuit pattern by the exposure apparatus. In the development step, the wafer exposed to light in the exposure step is developed. In the etching step, portions other than the developed resist image are etched. Then, in the resist removal step, any unnecessary resist remaining after etching is removed. Repeating these steps forms multiple circuit patterns on the wafer.

It is noted that some of the exemplary embodiments of the present invention may be configured as listed below:

1. A liquid immersion type exposure apparatus includes a droplet detector which detects droplets on a wafer. The droplet detector includes a droplet discriminating unit.

2. The droplet detector includes an image processing processor, storage device, or processing/determining unit, such as a central processing unit (CPU).

3. The droplet discriminating unit discriminates droplets from a device pattern or foreign matter on the wafer.

4. The droplet detector is disposed on either a wafer stage or wafer conveying device.

5. The droplet detector includes an illuminating unit which illuminates an exposed wafer and a light detecting unit which detects light reflected from the wafer.

6. The liquid immersion type exposure apparatus is configured such that a droplet remover which removes droplets on the wafer is disposed on either the wafer stage or wafer conveying device.

7. The droplet discriminating unit compares an image of an exposed wafer with a prestored image of a circuit pattern on the wafer to identify droplets. The prestored image may be generated, for example, on the basis of an original pattern having been used up to the present.

8. Alternatively, the droplet discriminating unit may compare an image of an exposed wafer with an image of an unexposed wafer captured by a camera serving as the light detecting unit and stored during wafer loading, thereby identifying droplets.

9. The droplet detector may include an illuminating unit using a laser beam, a light detecting unit using a line sensor, a signal processing system using a lowpass filter for processing an output of the light detecting unit. It is preferable in this case that the light detecting unit be defocused. The lowpass filter preferably has a bandwidth of less than or equal to 100 KHz and more preferably less than or equal to 10 KHz.

10. The droplet detector may include an illuminating unit which illuminates a wafer and a plurality of light detecting units which detect reflected light from the wafer via polarizers, and may be configured such that the plurality of light detecting units simultaneously receive P-polarized light and S-polarized light. In this case, a signal processing system determines a difference between a P-polarized light signal and an S-polarized light signal to detect droplets on the wafer. It is preferable that the angle of incidence be at about a Brewster's angle.

11. The droplet detector may be configured to use an infrared light source as an illuminating unit, use a light detecting element sensitive to infrared light as a light detecting unit, and identifies droplets on the basis of a spectrum obtained by the Fourier transform infrared spectroscopy method.

While the present invention has been described with reference to the exemplary embodiments, it is to be understood that the invention is not limited to the disclosed exemplary embodiments. The scope of the following claims is to be accorded the broadest interpretation so as to encompass all modifications, equivalent structures and functions.

This application claims priority from Japanese Patent Application No. 2006-239551, entitled "CONVEYING DEVICE, EXPOSURE APPARATUS, AND METHOD" and filed on Sep. 4, 2006, the entire contents of which are incorporated herein by reference.

What is claimed is:

1. An exposure apparatus comprising:
a movable substrate stage configured to hold a substrate;
an optical system configured to project light from an original, wherein the apparatus is configured to perform an exposure of the substrate to light via liquid filled in a gap between a last surface of the optical system and the substrate;
a detecting device configured to detect a droplet adhering to a surface of the substrate; and
a removing device arranged on the substrate stage and configured to remove the detected droplet at a substrate recovery position away from the optical system,
the detecting device including,
an image-capturing unit arranged on the substrate stage and configured to capture an image of a surface of the substrate, wherein the detecting device is configured to detect the droplet based on a comparison between first image data obtained by the image capturing unit while a substrate stage that holds an unexposed substrate is moved to a position under the optical system and second image data obtained by the image capturing unit while an exposure substrate stage that holds an exposed substrate is moved to the substrate recovery position, wherein size of the droplet is determined based on information on coordinates of the wafer stage and a spatial frequency bandwidth of a lowpass filter is determined based on the size of the droplet.

2. A method of manufacturing a device using the exposure apparatus according to claim 1,
the method comprising:
exposing the substrate to light using the exposure apparatus;
developing the exposed substrate; and
processing the developed substrate to manufacture the device.

3. The method according to claim 2, wherein the detecting device in the exposure apparatus includes:
an irradiating unit configured to irradiate a space along the surface of the substrate with light; and
a light detecting unit configured to detect light from the droplet.

4. The method according to claim 3, wherein the detecting device further includes a smoothing unit configured to smooth image data obtained from the light detecting unit.

5. The method according to claim 2, wherein the detecting device in the exposure apparatus includes:
an irradiating unit configured to irradiate the surface of the substrate with light;
a first light detecting unit configured to detect P-polarized light from the surface irradiated with light; and
a second light detecting unit configured to detect S-polarized light from the surface irradiated with light.

6. The method according to claim 5, wherein the detecting device detects the droplet based on a comparison between image data obtained by the first light detecting unit and the image data obtained by the second light detecting unit.

7. The apparatus according to claim 1, wherein the detecting device includes:
an irradiating unit configured to irradiate a space along the surface of the substrate with light; and
a light detecting unit configured to detect light from the droplet.

8. The apparatus according to claim 7, wherein the detecting device further includes a smoothing unit configured to smooth image data obtained from the light detecting unit.

9. The apparatus according to claim 1, wherein the detecting device includes:
an irradiating unit configured to irradiate the surface of the substrate with light;
a first light detecting unit configured to detect P-polarized light from the surface irradiated with light; and
a second light detecting unit configured to detect S-polarized light from the surface irradiated with light.

10. The apparatus according to claim 9, wherein the detecting device detects the droplet based on a comparison between image data obtained by the first light detecting unit and the image data obtained by the second light detecting unit.

* * * * *